(12) United States Patent
Shiraki et al.

(10) Patent No.: US 10,101,275 B2
(45) Date of Patent: Oct. 16, 2018

(54) PLASMA SPECTROCHEMICAL ANALYSIS METHOD AND PLASMA SPECTROCHEMICAL ANALYZER

(71) Applicant: ARKRAY, Inc., Kyoto (JP)

(72) Inventors: Yasunori Shiraki, Kyoto (JP); Hitoshi Okai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 13 days.

(21) Appl. No.: 14/994,277

(22) Filed: Jan. 13, 2016

(65) Prior Publication Data

US 2016/0202187 A1 Jul. 14, 2016

(30) Foreign Application Priority Data

Jan. 13, 2015 (JP) .................................. 2015-003795
Jan. 12, 2016 (JP) .................................. 2016-003555

(51) Int. Cl.
*G01J 3/30* (2006.01)
*G01N 21/68* (2006.01)
*G01N 33/20* (2006.01)
*G01N 21/67* (2006.01)

(52) U.S. Cl.
CPC ............. *G01N 21/68* (2013.01); *G01N 21/67* (2013.01); *G01N 33/20* (2013.01)

(58) Field of Classification Search
CPC ........ G01N 21/66; G01N 21/67; G01N 21/68; G01N 33/20
USPC ......................................................... 356/316
See application file for complete search history.

(56) References Cited

U.S. PATENT DOCUMENTS

| 3,144,551 A | 8/1964 | Webb et al. |
| 3,545,863 A | 12/1970 | Ault et al. |
| 6,710,870 B1 * | 3/2004 | Marowsky ......... G01N 21/6452 356/311 |
| 2002/0109841 A1 * | 8/2002 | Gould ...................... G01J 3/02 356/318 |

(Continued)

FOREIGN PATENT DOCUMENTS

| JP | 2009-128315 A | 6/2009 |
| JP | 2011-180045 A | 9/2011 |

(Continued)

OTHER PUBLICATIONS

Khoai et al, Development of high sensitive liquid electrode plasma-Atomic emission spectrometry (LEP-AES) integrated with solid phase pre-concentration, Microelectronic Engineering, vol. 111, Nov. 2013, pp. 343-347.*

(Continued)

*Primary Examiner* — Tarifur Chowdhury
*Assistant Examiner* — Jonathon Cook
(74) *Attorney, Agent, or Firm* — Morgan, Lewis & Bockius LLP (57) ABSTRACT

The present invention provides a plasma spectrochemical analysis method that can be carried out easily and achieves high analytical sensitivity, and includes: a step of concentrating an analyte in a sample in the vicinity of at least one of a pair of electrodes by applying a voltage to the pair of electrodes in the presence of the sample; and a step of generating plasma by applying a voltage to the pair of electrodes and detecting light emitted from the analyte excited by the plasma.

18 Claims, 4 Drawing Sheets

(56) References Cited

U.S. PATENT DOCUMENTS

| | | | | |
|---|---|---|---|---|
| 2003/0214651 A1* | 11/2003 | Hudak | ................... | G01N 21/68 |
| | | | | 356/316 |
| 2005/0012038 A1* | 1/2005 | Marcus | ..................... | G01J 3/10 |
| | | | | 250/288 |
| 2006/0043064 A1* | 3/2006 | Tanaka | .................. | G01N 21/68 |
| | | | | 216/61 |
| 2006/0285108 A1* | 12/2006 | Morrisroe | ............. | F23C 99/003 |
| | | | | 356/316 |
| 2009/0109141 A1 | 4/2009 | Murase et al. | | |
| 2009/0266984 A1* | 10/2009 | Hirano | .................... | H01J 37/14 |
| | | | | 250/288 |
| 2013/0148117 A1 | 6/2013 | Kulkarni et al. | | |
| 2013/0265574 A1* | 10/2013 | Buckley | ............. | G01N 15/0618 |
| | | | | 356/313 |
| 2013/0321803 A1 | 12/2013 | Kohara et al. | | |
| 2013/0321804 A1* | 12/2013 | Kulkarni | ................. | G01J 3/443 |
| | | | | 356/316 |

FOREIGN PATENT DOCUMENTS

| | | |
|---|---|---|
| JP | 2012-185064 A | 9/2012 |
| WO | 2006/059808 A1 | 6/2006 |
| WO | 2011/099247 A1 | 8/2011 |
| WO | 2012/048308 A2 | 4/2012 |

OTHER PUBLICATIONS

Extended European Search Report issued in corresponding European Patent Application No. 16151054.0 dated Jun. 2, 2016.

* cited by examiner

PLASMA SPECTROCHEMICAL ANALYSIS METHOD AND PLASMA SPECTROCHEMICAL ANALYZER

BACKGROUND OF THE INVENTION

1. Field of the Invention

The present invention relates to a plasma spectrochemical analysis method and a plasma spectrochemical analyzer.

2. Description of Related Art

As a method for analyzing an analyte in a sample, an analysis method utilizing plasma emission is known. Patent Document 1 discloses such a method for analyzing a sample using a high-frequency plasma mass spectrometer. Patent Documents 2 and 3 each disclose a method for analyzing a sample by generating plasma in the sample using a plasma generator having a narrow portion and analyzing the plasma emission. Patent Documents 4 and 5 each disclose a method for analyzing a liquid sample by generating plasma in the liquid sample and analyzing the plasma emission.

However, the method disclosed in Patent Document 1 has a problem in that, without a proper pretreatment of a sample, contamination of the sample with other substances may affect the result of analysis. The methods disclosed in Patent Documents 2 and 3 have a problem in that, when a liquid sample with impurities is used or when a foreign substance (s) or the like is mixed in the liquid sample during a pretreatment for reducing the amount of the liquid sample, the narrow portion is clogged with the impurities or foreign substance(s), thus making measurement impossible. The methods disclosed in Patent Documents 4 and 5 have a problem in that they are only able to achieve low analytical sensitivity.

CITATION LIST

Patent Document(s)

Patent Document 1: JP 2009-128315 A
Patent Document 2: JP 2011-180045 A
Patent Document 3: JP 2012-185064 A
Patent Document 4: WO 2006/059808
Patent Document 5: WO 2011/099247

BRIEF SUMMARY OF THE INVENTION

Problem to be Solved by the Invention

With the foregoing in mind, it is an object of the present invention to provide a plasma spectrochemical analysis method that can be carried out easily and can achieve high analytical sensitivity.

Means for Solving Problem

In order to achieve the above object of the present invention, the present invention provides a plasma spectrochemical analysis method (also referred to simply as "analysis method" hereinafter) comprising: a concentration step of concentrating an analyte in a sample in the vicinity of at least one of a pair of electrodes by applying a voltage to the pair of electrodes in the presence of the sample; and a detection step of generating plasma by applying a voltage to the pair of electrodes and detecting light emitted from the analyte excited by the plasma.

The present invention also provides a plasma spectrochemical analyzer (also referred to simply as "analyzer" hereinafter) for use in the plasma spectrochemical analysis method according to the present invention, comprising: a pair of electrodes; a container; and a light receiving part, wherein the container includes a light transmitting part, the pair of electrodes are disposed in the container, and the light receiving part is disposed outside the container in such a manner that the light receiving part can receive light emitted from an analyte by applying a voltage to the pair of electrodes via the light transmitting part.

Effects of the Invention

The plasma spectrochemical analysis method of the present invention can be carried out easily and can achieve high analytical sensitivity. Thus, according to the plasma spectrochemical analysis method of the present invention, it is possible to analyze a sample easily with high sensitivity, without performing a pretreatment of the sample, for example.

DETAILED DESCRIPTION OF THE INVENTION (Plasma Spectrochemical Analysis Method)

As described above, the plasma spectrochemical analysis method of the present invention comprises: a concentration step of concentrating an analyte in a sample in the vicinity of at least one of a pair of electrodes by applying a voltage to the pair of electrodes in the presence of the sample; and a detection step of generating plasma by applying a voltage to the pair of electrodes and detecting light emitted from the analyte excited by the plasma. The analysis method of the present invention is characterized in that it includes the above-described concentration step and detection step, and other steps and conditions are not particularly limited.

A method commonly used in the art to perform efficient analysis of an analyte in a sample is, for example, to pretreat the sample so as to reduce the total volume (the total liquid volume) of the sample by concentrating the sample, thereby increasing the amount of the analyte per unit volume of the whole sample. However, according to the present invention, a pretreatment step for reducing the total volume of a sample is not necessary for the following reason. Specifically, according to the analysis method of the present invention, if the total volume of a sample is not reduced, an analyte in the sample is concentrated in the vicinity of at least one of a pair of electrodes by applying a voltage to the pair of electrodes in the concentration step. In other words, the analyte can be accumulated locally in the vicinity of the electrode. Thus, in the subsequent detection step, by generating plasma on the side of the electrode around which the analyte has been accumulated, the analyte present locally at a high concentration can be analyzed efficiently. Therefore, according to the analysis method of the present invention, for example, even when a sample to be used contains an analyte at a low concentration, the sample can be analyzed easily with high sensitivity without pretreating the sample prior to the analysis, for example. Furthermore, because the analysis method of the present invention can achieve efficient analysis by accumulating an analyte in the vicinity of at least one of a pair of electrodes and then generating plasma on that particular side of the electrode, an analyzer having a narrow portion as described in the above-described prior art documents is not essential to carry out the analysis method of the present invention. Therefore, for example, the above-described problem such as clogging of the analyzer with impurities present in the sample can be avoided, and the analysis is thus not significantly affected by impurities. Therefore, according to the analysis method of the present invention, even when a sample contains impurities, for example, it is not necessary to perform a pretreatment step or the like to remove impurities that may be present.

In the analysis method of the present invention, the sample may be a specimen, for example. The specimen may be either liquid or solid. The specimen may be used as a liquid specimen as it is without being diluted, or a diluted solution obtained by suspending, dispersing, or dissolving the specimen in a medium may be used as a liquid specimen, for example. When the specimen is solid, it is preferable to use a diluted solution obtained by suspending, dispersing, or dissolving the specimen in a medium as a liquid specimen, for example. The medium is not particularly limited, and examples thereof include water and buffer solutions. The specimen may be, for example, a specimen (sample) derived from a biological source (hereinafter referred to as "biological specimen (sample)"); a specimen (sample) derived from an environmental source (hereinafter referred to as "environmental specimen (sample)"); a metal; a chemical substance; or a pharmaceutical. The biological specimen is not particularly limited, and may be urine, blood, hair, saliva, sweat, nails, or the like. The blood specimen may be, for example, erythrocytes, whole blood, serum, or plasma. The biological source may be, for example, a human, a non-human animal, or a plant. Examples of the non-human animal include: mammals excluding humans; fish; and shellfish. The environmental specimen is not particularly limited, and may be, for example, a food, water, soil, atmospheric air, or air in general. The food may be, for example, a fresh food or a processed food. The water may be, for example, drinking water, underground water, river water, sea water, or domestic wastewater.

The analyte is not particularly limited, and may be a metal or a chemical substance, for example. The metal is not particularly limited, and examples thereof include aluminum (Al), antimony (Sb), arsenic (As), barium (Ba), beryllium (Be), bismuth (Bi), cadmium (CO cesium (Cs), gadolinium (Gd), lead (Pb), mercury (Hg), nickel (Ni), palladium (Pd), platinum (Pt), tellurium (Te), thallium (Tl), thorium (Th), tin (Sn), tungsten (W), and uranium (U). Examples of the chemical substance include reagents, agricultural chemicals, and cosmetics. The analysis method of the present invention may analyze one kind of analyte, or two or more kinds of analytes, for example.

When the analyte is a metal, the sample may contain a reagent for separating the metal contained in the specimen, for example. The reagent may be, for example, a chelating agent or a masking agent. Examples of the chelating agent include dithizone, tiopronin, meso-2,3-dimercaptosuccinic acid (DMSA), 2,3-dimercapto-1-propanesulfonic acid sodium salt (DMPS), ethylenediaminetetraacetic acid (EDTA), nitrilotriacetic acid (NTA), ethylenediamine-N,N'-disuccinic acid (EDDS), and α-lipoic acid. In the present invention, "masking" means to inactivate the reactivity of a SH group, and this can be achieved by chemical modification of the SH group, for example. Examples of the masking agent include maleimide, N-methylmaleimide, N-ethylmaleimide, N-phenylmaleimide, maleimidopropionic acid, iodoacetamide, and iodoacetic acid.

The sample may be, for example, a sample the pH of which has been adjusted (also referred to as "pH-adjusted sample" hereinafter). The pH of the pH-adjusted sample is not particularly limited. The method for adjusting the pH of the sample is not particularly limited, and the adjustment can be achieved with the use of a pH adjusting reagent such as an alkaline reagent or an acidic reagent, for example.

The alkaline reagent may be, for example, an alkali or an aqueous solution thereof. The alkali is not particularly limited, and examples thereof include sodium hydroxide, lithium hydroxide, potassium hydroxide, and ammonia. The aqueous solution of the alkali can be obtained by diluting the alkali with water or a buffer solution, for example. In the aqueous solution of the alkali, the concentration of the alkali is not particularly limited, and may be 0.01 to 5 mol/L, for example.

The acidic reagent may be, for example, an acid or an aqueous solution thereof. The acid is not particularly limited, and examples thereof include hydrochloric acid, sulfuric acid, acetic acid, boric acid, phosphoric acid, citric acid, malic acid, succinic acid, and nitric acid. The aqueous solution of the acid can be obtained by diluting the acid with water or a buffer solution, for example. In the aqueous solution of the acid, the concentration of the acid is not particularly limited, and may be 0.01 to 5 mol/L, for example.

Each of the electrodes is not particularly limited, and may be, for example, a solid electrode. A specific example of the electrode is a rod electrode. The material of the electrode is not particularly limited as long as it is a solid conductive material, and can be determined as appropriate depending on the kind of the analyte, for example. The material of the electrode may be, for example, a nonmetal, a metal, or a mixture thereof. When the material of the electrode is a nonmetal-containing material, the material of the electrode may contain one kind of nonmetal or two or more kinds of nonmetals, for example. Examples of the nonmetal include carbon. When the material of the electrode is a metal-containing material, the material of the electrode may contain one kind of metal or two or more kinds of metals, for example. Examples of the metal include gold, platinum, copper, zinc, tin, nickel, palladium, titanium, molybdenum, chromium, and iron. When the material of the electrode contains two or more kinds of metals, the material of the electrode may be an alloy. Examples of the alloy include brass, steel, Inconel®, nichrome, and stainless steel. The pair of electrodes may be formed of the same material or different materials, for example.

The size of each electrode is not particularly limited as long as the electrode can be in contact with the sample, for example. When the electrode is a rod electrode, the diameter of the electrode is, for example, 0.02 to 50 mm or 0.05 to 5 mm, and the length of the electrode is, for example, 0.1 to 200 mm or 0.3 to 50 mm. The sizes of the pair of electrodes may be the same or different from each other.

As described above, the concentration step is the step of concentrating an analyte in a sample in the vicinity of at least one of a pair of electrodes by applying a voltage to the pair of electrodes in the presence of the sample. The sample is in contact with a pair of electrodes, for example. In the concentration step, the vicinity of the electrode is not particularly limited, and may be, for example, a region where plasma is generated in the detection step to be described below. In the present invention, the vicinity of the electrode also encompasses a region on the electrode, for example.

In the concentration step, for example, part of the analyte may be concentrated in the vicinity of the electrode, or the entire analyte may be concentrated in the vicinity of the electrode.

In the concentration step, the electric charge condition of the pair of electrodes preferably is set so that the analyte is concentrated in the vicinity of the electrode used for detection of the analyte (i.e., the electrode for plasma generation) in the detection step to be described below. The electric charge condition is not particularly limited, and may be as follows, for example: when the analyte is positively charged, the electric charge condition may be set so that the electrode for plasma generation is negatively charged; and when the analyte is negatively charged, the electric charge condition may be set so that the electrode for plasma generation is positively charged.

The concentration of the analyte can be controlled by a voltage, for example. Thus, those skilled in the art can set a voltage at which the concentration occurs (also referred to as "concentration voltage" hereinafter) as appropriate. The concentration voltage is, for example, at least 1 mV or at least 400 mV, and the upper limit thereof is not particularly limited. The concentration voltage may be constant or may be varied, for example. Also, the concentration voltage may be a voltage at which plasma generation does not occur, for example.

The time period for which the concentration voltage is applied is not particularly limited, and can be set as appropriate depending on the concentration voltage. The time period for which the concentration voltage is applied is, for example, 0.2 to 40 minutes or 1 to 5 minutes. The voltage may be applied to the pair of electrodes either continuously or discontinuously, for example. Examples of the discontinuous voltage application include pulse application. When the voltage is applied discontinuously, the time period for which the concentration voltage is applied may be, for example: the total of the time periods for which the concentration voltage is applied; or the total of the time periods for which the concentration voltage is applied and the time period(s) for which the concentration voltage is not applied.

The voltage application to the electrodes can be carried out using voltage application means. The voltage application means is not particularly limited as long as it can apply a voltage between the electrodes, for example, and known means such as a voltage generator can be used. In the concentration step, a current between the electrodes can be set to 0.01 to 200 mA, 10 to 60 mA, or 10 to 40 mA, for example.

As described above, the detection step is the step of generating plasma by applying a voltage to the pair of electrodes and detecting light emitted from the analyte excited by the plasma.

The detection step may or may not be performed successively to the concentration step. When the detection step is performed successively to the concentration step, the detection step is started immediately after the completion of the concentration step. When the detection step is not performed successively to the concentration step, the detection step is performed within a predetermined time after the completion of the concentration step. The predetermined time is, for example, within 0.001 to 1000 seconds or 1 to 10 seconds after the completion of the concentration step.

In the detection step, "generating plasma" means to generate plasma substantially. Specifically, it means generating plasma that causes substantially detectable light emission in the detection of plasma emission. As a specific example, it means generating plasma that causes plasma emission detectable with a plasma emission detector.

Substantial plasma generation can be controlled by a voltage, for example. Thus, those skilled in the art can set a voltage for generating plasma that causes substantially detectable light emission (also referred to as "plasma voltage" hereinafter) as appropriate. The plasma voltage is, for example, at least 10 V or at least 100 V, and the upper limit thereof is not particularly limited. A voltage at which the plasma generation occurs is relatively higher that a voltage at which the concentration occurs, for example. Thus, the plasma voltage preferably is set so as to be higher than the concentration voltage. The plasma voltage may be constant or may be varied, for example.

The time period for which the plasma voltage is applied is not particularly limited, and can be set as appropriate depending on the plasma voltage. The time period for which the plasma voltage is applied is, for example, 0.001 to 0.02 seconds or 0.001 to 0.01 seconds. The voltage may be applied to the pair of electrodes either continuously or discontinuously, for example. Examples of the discontinuous voltage application include pulse application. When the voltage is applied discontinuously, the time period for which the plasma voltage is applied may be, for example: the time period for a single application of the plasma voltage; the total of the time periods for which the plasma voltage is applied; or the total of the time periods for which the plasma voltage is applied and the time period(s) for which the plasma voltage is not applied.

In the detection step, setting of the electrode for plasma generation can be controlled by the difference in contact area with the sample between the pair of electrodes, for example. Specifically, with the configuration in which one of the electrodes has a smaller contact area than the other electrode, the former electrode can serve as an electrode for plasma generation. Thus, in the present invention, it is preferable that contact areas of the electrodes with the sample are different from each other, and the electrode having a smaller contact area with the sample is used as an electrode for analyzing an analyte by plasma generation. When the contact areas of the pair of electrodes are different from each other, the difference between the contact areas of the pair of electrodes is, for example, 0.001 to 300 $cm^2$ or 1 to 10 $cm^2$. In the present invention, the term "contact area" refers to the area in contact with the sample. The method for adjusting the contact areas is not particularly limited, and examples thereof include: immersing the electrodes in the sample in such a manner that the lengths of the immersed portions of the electrodes are different from each other; and coating part of a contact portion of one of the electrodes with the sample with an insulating material. The insulating material is not particularly limited, and examples thereof include resins, silicones, glass, paper, ceramics, and rubbers. Examples of the resins include: thermoplastic resins such as polyethylene, polypropylene, polystyrene, polyvinyl chloride, polyethylene terephthalate, polymethacrylate, polyamide, saturated polyester resins, acrylic resins, polybutylene terephthalate (PBT), polyetheretherketone (PEEK), and polymethylpentene (for example, TPX®); and thermosetting resins such as urea resins, melamine resins, phenol resins, fluororesins, epoxy resins (e.g., glass epoxy), and unsaturated polyester resins. Examples of the silicones include polydimethylsiloxane.

In the detection step, light emission caused by the generated plasma may be detected continuously or discontinuously, for example. Detection of the light emission is, for example, detection of the presence or absence of the light emission, detection of the intensity of the light emission, or detection of a specific wavelength, or detection of a spectrum. The detection of a specific wavelength is, for example, detection of a wavelength characteristic of plasma emission of the analyte. The method for detecting the light emission is not particularly limited, and a known optical measuring instrument such as a charge coupled device (CCD) or a spectroscope can be used, for example.

The voltage application to the electrodes can be carried out using voltage application means. Regarding the voltage application means, reference can be made to the above description relating to the voltage application means, for example. In the detection step, a current between the electrodes can be set to 0.01 to 100000 mA or 50 to 2000 mA, for example.

The analysis method of the present invention further may include a calculation step of calculating the concentration of the analyte in the sample from the detection result obtained in the detection step. The detection result may be the above-described light emission intensity or the like, for example. In the calculation step, the concentration of the analyte can be calculated on the basis of the detection result and the correlation between the detection result and the concentration of the analyte in the sample, for example. The correlation can be determined by carrying out detection with regard to standard samples with known concentrations of the analyte by the analysis method of the present invention, and plotting the detection results and the concentrations of the analyte in the standard samples, for example. The standard samples preferably are a dilution series of the analyte. By carrying out the calculation as described above, highly reliable quantification became possible.

In the analysis method of the present invention, the pair of electrodes may be disposed in a container that includes a light transmitting part. In this case, in the detection step, the emitted light is detected by a light receiving part disposed in such a manner that it can receive light emitted from the analyte via the light transmitting part. For the details of the container, the light transmitting part, the light receiving part, etc., reference can be made to descriptions relating to these components provided below in connection with the analyzer of the present invention, for example.

(Plasma Spectrochemical Analyzer)

As described above, the plasma spectrochemical analyzer of the present invention is a plasma spectrochemical analyzer for use in the plasma spectrochemical analysis method according to the present invention, comprising: a pair of electrodes; a container; and a light receiving part, wherein the container includes a light transmitting part, the pair of electrodes are disposed in the container, and the light receiving part disposed outside the container in such a manner that the light receiving part can receive light emitted from an analyte by applying a voltage to the pair of electrodes via the light transmitting part. The analyzer of the present invention is characterized in that it is used in the analysis method of the present invention, and other configurations and conditions are not particularly limited. According to the analyzer of the present invention, the analysis method of the present invention can be carried out easily. The description regarding the analyzer of the present invention and the description regarding the analysis method of the present invention may be mutually referenced, for example.

An example of the analyzer of the present invention will be described with reference to the drawings. In the drawings, the structure of each component may be shown in an simplified form as appropriate for the sake of convenience in illustration, and also, each component may be shown schematically with a dimension ratio and the like that are different from the actual dimension ratio and the like.

Figure 1A:
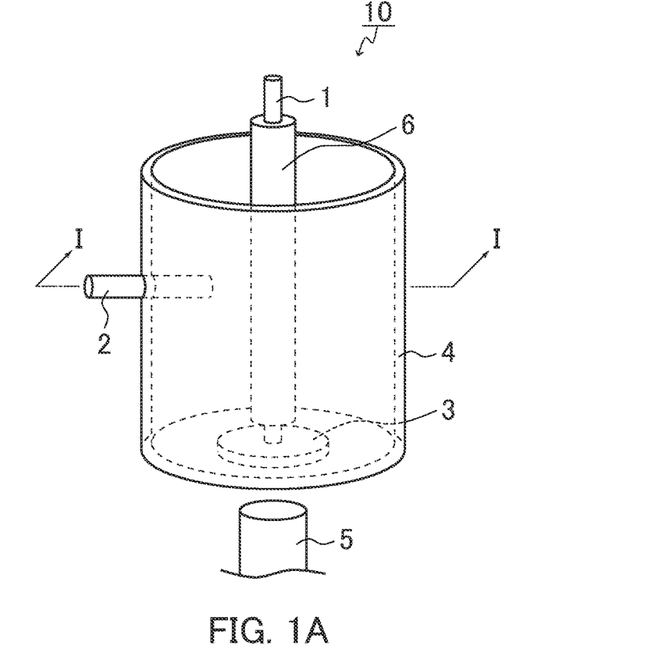
FIG. 1A is a schematic see-through perspective view of an analyzer according to an embodiment of the present invention.
Figure 1B:
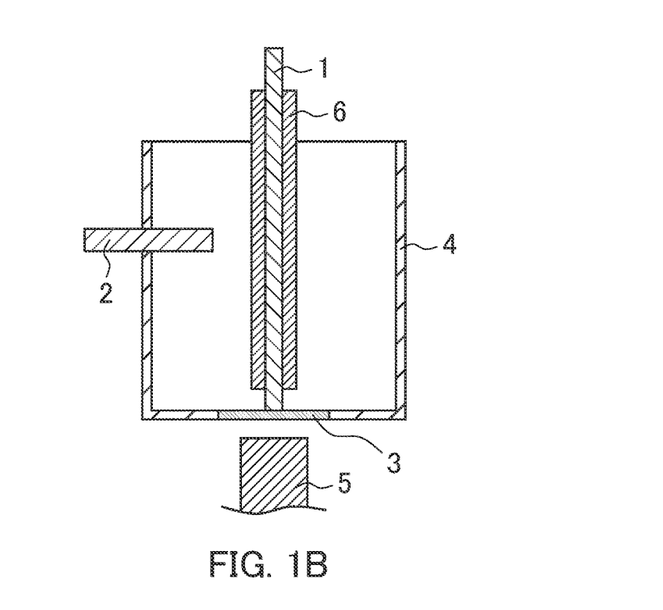
FIG. 1B is a schematic sectional view of the analyzer, viewed along arrows I-I in FIG. 1A.

FIG. 1A is a schematic see-through perspective view of an analyzer of the present embodiment, and FIG. 1B is a schematic sectional view of the analyzer, viewed along arrows I-I in FIG. 1A. As shown in FIGS. 1A and 1B, an analyzer 10 of the present embodiment includes a pair of electrodes 1 and 2, a container 4, and a light receiving part 5. The container 4 includes a light transmitting part 3. The light receiving part 5 is disposed outside the container 4 in such a manner that it can receive light emitted from an analyte by applying a voltage to the pair of electrodes 1 and 2 via the light transmitting part 3. The electrode 1 is disposed so that it extends perpendicularly to the bottom surface of the container 4, and the tip of the electrode 1 is in contact with the light transmitting part 3. The electrode 2 extends so as to pass through the side surface of the container 4 toward the inside of the container 4. The electrode 1 is coated with an insulating material 6. In the analyzer 10 of the present embodiment, a sample containing an analyte is introduced into the container 4 so that the sample is in contact with the electrodes 1 and 2, for example. In the present embodiment, the analyzer 10 is a vertical placement type analyzer. However, the analyzer 10 is not limited thereto, and may be a horizontal placement type analyzer, for example.

In the present embodiment, the surface of the electrode 1 is partially coated with the insulating material 6. However, the insulating material 6 is an optional component, and may or may not be used. In the present embodiment, the electrodes 1 and 2 are disposed on different surfaces of the container 4. However, the positions at which the electrodes 1 and 2 are disposed are not particularly limited, and the electrodes 1 and 2 may be disposed at any positions, for example.

In the present embodiment, the electrode 1 is in contact with the light transmitting part 3. However, the present invention is not limited thereto. For example, the electrode 1 and the light transmitting part 3 may be disposed so as to be apart from each other. The distance between the electrode 1 and the bottom surface of the container 4 is not particularly limited, and is, for example, 0 to 2 cm or 0 to 0.5 cm.

The material of the light transmitting part 3 is not particularly limited as long as light emitted as a result of voltage application to the pair of electrodes 1 and 2 can be transmitted through the light transmitting part 3, for example, and can be set as appropriate depending on the wavelength of the emitted light. Examples of the material of the light transmitting part 3 include quartz glass, acrylic resins (PMMA), borosilicate glass, polycarbonates (PC), cycloolefin polymers (COP), and methylpentene polymers (TPX®). The size of the light transmitting part 3 is not particularly limited as long as light emitted as a result of voltage application to the pair of electrodes 1 and 2 can be transmitted through the light transmitting part 3, for example.

In the present embodiment, the container 4 has a bottomed cylindrical shape. However, the shape of the container 4 is not limited thereto, and the container 4 may have any shape. The material of the container 4 is not particularly limited, and examples thereof include acrylic resins (PMMA), polypropylene (PP), polyethylene (PE), polyvinyl chloride (PVC), polyethylene terephthalate (PET), and polystyrene (PS). The volume of the container 4 is, for example, 0.3 to 0.5 $cm^3$. In the case where the container 4 has a bottomed cylindrical shape, the diameter of the container 4 is, for example, 0.4 to 50 cm or 1 to 5 cm, and the height of the container 4 is, for example, 0.3 to 50 cm or 0.7 to 2 cm.

The light receiving part 5 is not particularly limited, and examples thereof include known optical measuring instruments such as CCD and spectroscopes. Alternatively, the light receiving part 5 may be transmission means for transmitting the emitted light to the optical measuring instrument disposed outside the analyzer 10, for example. The transmission means may be, for example, a transmission path such as an optical fiber.

The method for producing the container 4 is not particularly limited. For example, the container 4 may be produced by obtaining a molded product by injection molding or the like, or by forming a recess in a base such as a plate. Other examples of the method for producing the container 4, etc. include, but not particularly limited to, lithography and cutting.

EXAMPLES

Next, examples of the present invention will be described. It is to be noted, however, that the present invention is by no means limited by the following examples.

Example 1

The present example examined whether the analysis method of the present invention can analyze mercury with high sensitivity.

(1) Plasma Spectrochemical Analyzer

The analyzer according to the above-described embodiment was provided. Specifically, a bottomed cylindrical container formed of transparent PMMA (height: 15 mm×diameter: ϕ10 mm) was provided. At the center of the bottom of the container, a quartz glass member was disposed. An electrode 1 and an electrode 2 were disposed in the container. The electrode 1 was disposed in such a manner that it extended perpendicular to the bottom surface of the container and the tip of the electrode 1 was in contact with the quartz glass member at the bottom of the container. As the electrode 1, a brass rod with a diameter of 0.12 mm was used. The electrode 1 was configured so that a portion of 0.3 mm length from the tip was exposed and the remaining portion was insulated. The electrode 2 was disposed in such a manner it passed through the side surface of the container 4 toward the inside of the container 4 and extended perpendicular to the electrode 1. As the electrode 2, a carbon electrode rod with a diameter of 2.5 mm was used. An optical fiber was disposed so that it faced the tip of the electrode 1 with the quartz glass member therebetween. As the optical fiber, a single-core optical fiber with a diameter of 400 μm was used. The optical fiber was connected to a concave grating spectroscope (self-prepared).

(2) Plasma Spectrochemical Analysis

In 0.3 mL of 0.1 mol/L nitric acid aqueous solution, mercury chloride was dissolved at a concentration of 100 ppb. The resultant mixture was used as a mercury sample. Then, the mercury sample was introduced into the container of the analyzer. Subsequently, a voltage was applied between the electrode 1 and the electrode 2 under the following concentration conditions so that the electrode 1 served as a cathode and the electrode 2 served as an anode, whereby the mercury was concentrated in the vicinity of the electrode 1.

(Concentration Conditions)
Applied voltage: 30 V and 0 V repeatedly
Pulse width: 50 μs
Duty: 99%
Application time: 500 ms
The number of application times: 250 times at time interval of 1 s Immediately after the concentration, a voltage and a current were further applied between the electrode 1 and the electrode 2 under the following plasma generation conditions so that the electrode 1 served as a cathode and the electrode 2 served as an anode, and the emission intensity (the number of counts) of the generated plasma emission was measured at each wavelength. Also, as a control (comparative example), the spectrum of the generated plasma emission was measured in the same manner, except that the concentration was not performed.

Figure 2:
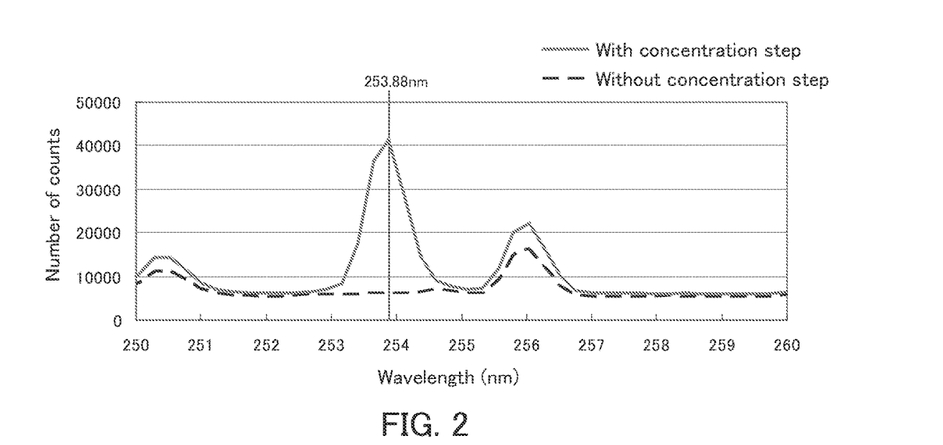
FIG. 2 is a graph showing spectra in the vicinity of the mercury peak in Example 1 of the present invention.

(Plasma Generation Conditions)
Applied voltage: 150 V and 0 V repeatedly
Pulse width: 50 μs
Duty: 80%
Application time: 100 ms The results thereof are shown in FIG. 2. FIG. 2 is a graph showing spectra in the vicinity of the mercury peak. In FIG. 2, the horizontal axis indicates the wavelength, and the vertical axis indicates the emission intensity (the number of counts). In FIG. 2, the solid line shows the result obtained regarding the example, and the dashed line shows the result obtained regarding the comparative example. As can be seen from FIG. 2, in the example, the number of counts increased in the vicinity of 253.65 nm, which is the wavelength of plasma emission characteristic of mercury, as compared with the comparative example. In FIG. 2, the peak (mercury peak) is observed at 253.88 nm. This is because the measured value includes a measurement error caused by the spectroscope. These results demonstrate that the analysis method of the present invention achieves higher analytical sensitivity than the analysis methods disclosed in Patent Documents 4 and 5, in which the concentration is not performed.

(3) Plasma Spectrochemical Analysis with Respect to Different Concentrations of Analyte The number of counts at the mercury peak was measured in the same manner as in (2) of Example 1, except that mercury chloride was dissolved in 0.3 mL of 0.1 mol/L nitric acid aqueous solution at a predetermined concentration (10 ppb, 50 ppb, or 100 ppb).

Figure 3:
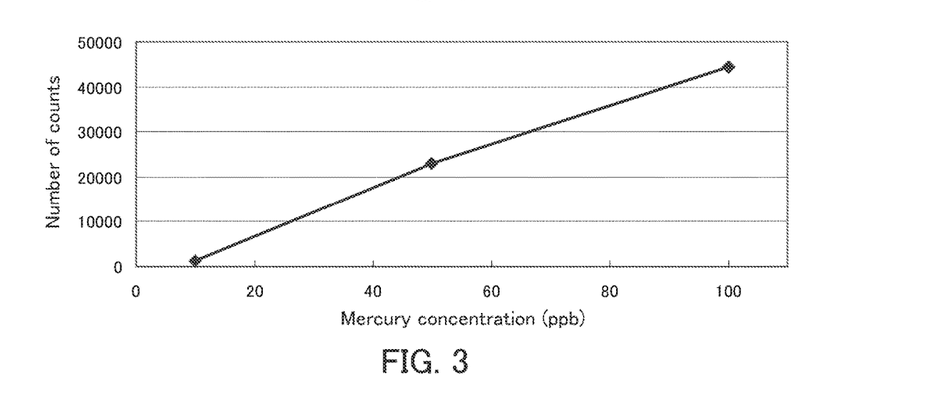
FIG. 3 is a graph showing the correlation between the mercury concentration and the number of counts at the mercury peak in Example 1 of the present invention.

The results thereof are shown in FIG. 3. FIG. 3 is a graph showing the correlation between the mercury concentration and the number of counts at the mercury peak. In FIG. 3, the horizontal axis indicates the mercury concentration, and the vertical axis indicates the emission intensity (the number of counts). As can be seen from FIG. 3, the number of counts increased in a mercury concentration dependent manner.

These results demonstrate that the analysis method of the present invention can analyze an analyte in a wide concentration range.

Example 2

The present example examined whether the analysis method of the present invention can analyze lead in a urine specimen with high sensitivity.

(1) Plasma Spectrochemical Analysis

Lead was dissolved in a urine specimen at a concentration of 100 ppb. Thereafter, lithium hydroxide powder was added thereto so that the concentration of lithium hydroxide was 0.2 mol/L. Then, the spectrum of the generated plasma emission was measured in the same manner as in (2) of Example 1, except that the thus-obtained lead sample was used instead of the mercury sample. Also, as a control (comparative example), the spectrum of the generated plasma emission was measured in the same manner, except that the concentration was not performed.

Figure 4:
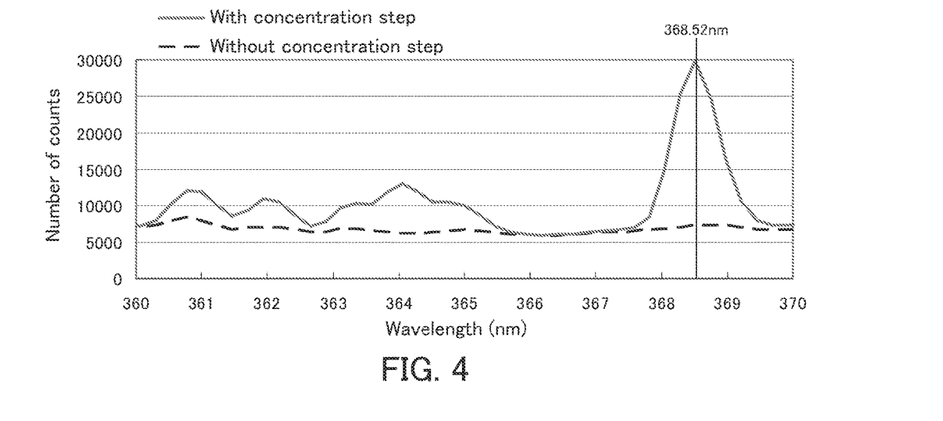
FIG. 4 is a graph showing spectra in the vicinity of the lead peak in Example 2 of the present invention.

The results thereof are shown in FIG. 4. FIG. 4 is a graph showing spectra in the vicinity of the lead peak. In FIG. 4, the horizontal axis indicates the wavelength, and the vertical axis indicates the emission intensity (the number of counts). In FIG. 4, the solid line shows the result obtained regarding the example, and the dashed line shows the result obtained regarding the comparative example. As can be seen from FIG. 4, in the example, the number of counts increased in the vicinity of 368.34 nm, which is the wavelength of plasma emission characteristic of lead, as compared with the comparative example. In FIG. 4, the peak (lead peak) is observed at 368.52 nm. This is because the measured value includes a measurement error caused by the spectroscope. These results demonstrate that the analysis method of the present invention achieves higher analytical sensitivity than the analysis methods disclosed in Patent Documents 4 and 5, in which the concentration is not performed.

(2) Plasma Spectrochemical Analysis with Respect to Different Concentrations of Analyte Lead nitrate was dissolved in a urine specimen at a predetermined concentration (10 ppb, 50 ppb, or 100 ppb). Thereafter, lithium hydroxide powder was added thereto so that the concentration of lithium hydroxide was 0.2 mol/L. The number of counts at the lead peak was measured in the same manner as in (2) of Example 1, except that the thus-obtained lead sample was used instead of the mercury sample.

Figure 5:
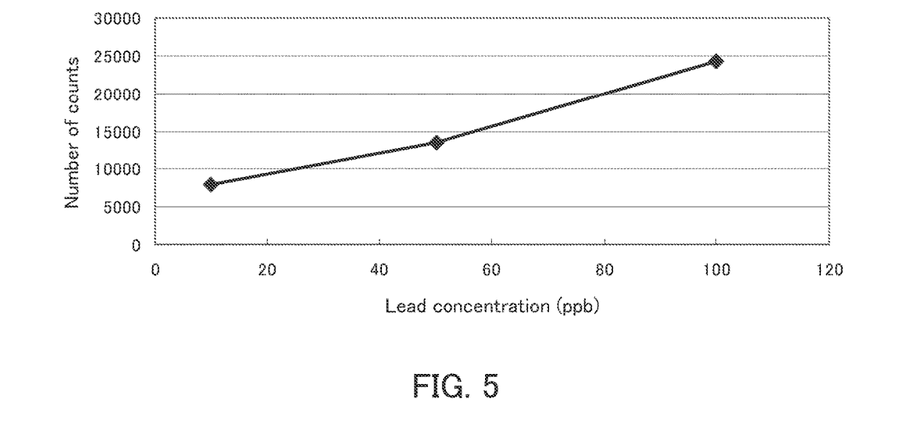
FIG. 5 is a graph showing the correlation between the lead concentration and the number of counts at the lead peak in Example 2 of the present invention.

The results thereof are shown in FIG. 5. FIG. 5 is a graph showing the correlation between the lead concentration and the number of counts at the lead peak. In FIG. 5, the horizontal axis indicates the lead concentration, and the vertical axis indicates the emission intensity (the number of counts). As can be seen from FIG. 5, the number of counts increased in a lead concentration dependent manner. These results demonstrate that the analysis method of the present invention can analyze an analyte in a wide concentration range. Also, it was found that the analysis method of the present invention can analyze an analyte even when the analyte is contained in a sample with impurities, such as a urine specimen.

Example 3

The present example examined whether the analysis method of the present invention can analyze cadmium with high sensitivity.

A cadmium sample was prepared by dissolving cadmium in 0.2 mol/L lithium hydroxide solution at a concentration of 1 ppm. The spectrum of the generated plasma emission was measured in the same manner as in (1) of Example 2, except that the thus-obtained cadmium sample was used instead of the lead sample. Also, as a control (comparative example), the spectrum of the generated plasma emission was measured in the same manner, except that the concentration was not performed.

Figure 6:
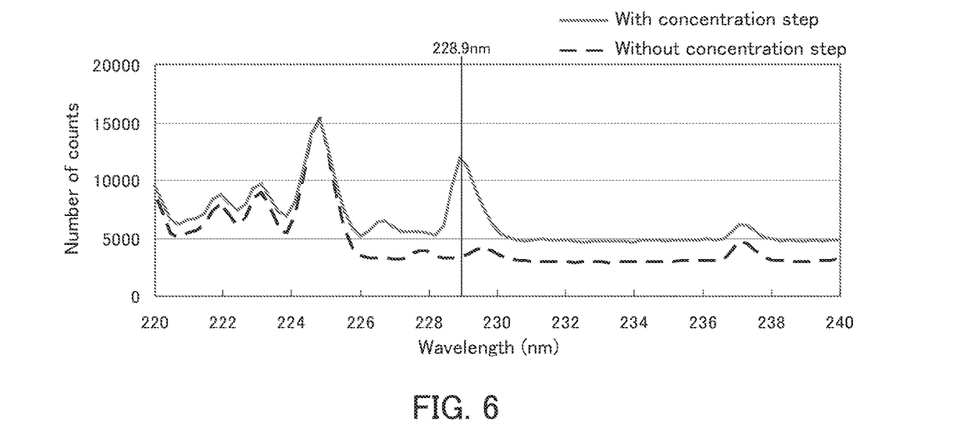
FIG. 6 is a graph showing spectra in the vicinity of the cadmium peak in Example 3 of the present invention.

The results thereof are shown in FIG. 6. FIG. 6 is a graph showing spectra in the vicinity of the cadmium peak. In FIG. 6, the horizontal axis indicates the wavelength, and the vertical axis indicates the emission intensity (the number of counts). In FIG. 6, the solid line shows the result obtained regarding the example, and the dashed line shows the result obtained regarding the comparative example. As can be seen from FIG. 6, in the example, the number of counts increased in the vicinity of 228.80 nm, which is the wavelength of plasma emission characteristic of cadmium, as compared with the comparative example. In FIG. 6, the peak is observed at 228.9 nm. This is because the measured value includes a measurement error caused by the spectroscope. These results demonstrate that the analysis method of the present invention achieves higher analytical sensitivity than the analysis methods disclosed in Patent Documents 4 and 5, in which the concentration is not performed.

Example 4

The present example examined whether the analysis method of the present invention can analyze mercury with high sensitivity.

The spectrum of the generated plasma emission was measured in the same manner as in (2) of Example 1, except that the mercury sample was prepared by dissolving mercury chloride in 0.3 mL of 0.1 mol/L nitric acid aqueous solution at a concentration of 10 ppb. Also, as Control 1 (Comparative Example 1), the spectrum of the generated plasma emission was measured in the same manner, except that the concentration was not performed.

As Control 2 (Comparative Example 2), a mercury sample was prepared by dissolving mercury in 0.3 mL of 0.1 mol/L nitric acid aqueous solution at a concentration of 5 ppm. Also, in Control 2, instead of the plasma spectrochemical analyzer, a resin cell having a narrow portion (LepiCuve, Micro Emission Ltd.) and a plasma spectrochemical analyzer (Ultra Compact Elemental Analyzer MH-500, Micro Emission Ltd.) for the resin cell measurement were used, and the spectrum of the plasma emission generated in the mercury sample was measured in accordance with the protocol attached to the plasma spectrochemical analyzer. As Control 3 (Comparative Example 3), the spectrum of the generated plasma emission was measured in the same manner as in Control 2, except that 0.1 mol/L nitric acid aqueous solution was used instead of the mercury sample and that a plasma spectrochemical analyzer compatible with the resin cell was used.

Figure 7A:
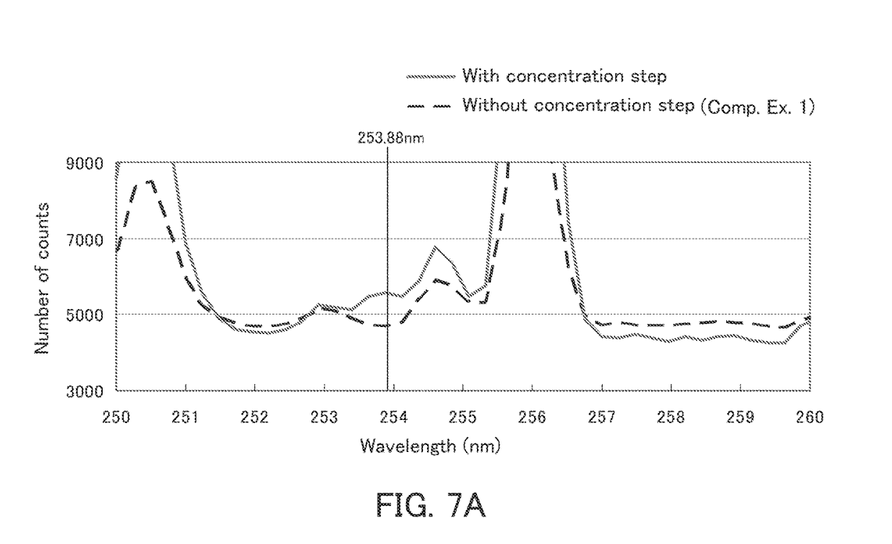
FIG. 7A is a graph showing spectra obtained when a 10 ppb mercury solution was analyzed in Example 4 of the present invention.
Figure 7B:
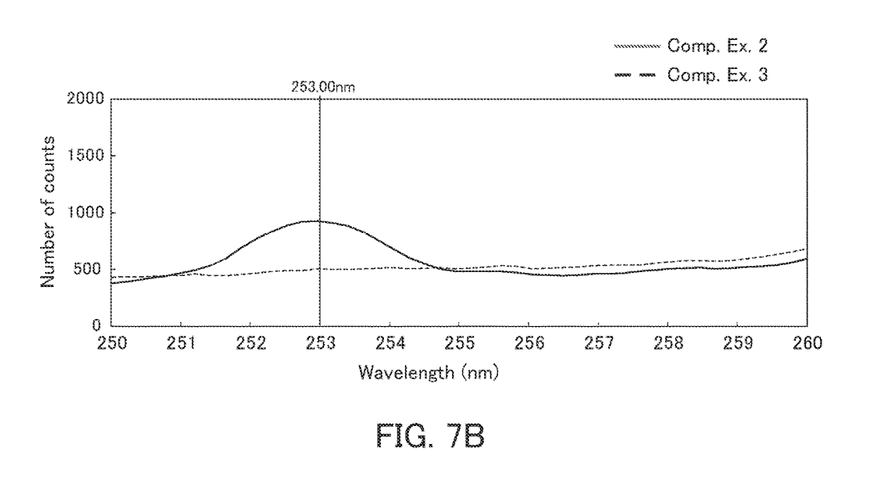
FIG. 7B is a graph showing spectra obtained when a 5 ppm mercury solution was analyzed using an analyzer having a narrow portion.

The results thereof are shown in FIGS. 7A and 7B. FIG. 7A is a graph showing spectra obtained when the 10 ppb mercury solution was analyzed, and FIG. 7B is a graph showing spectra obtained when the 5 ppm mercury solution was analyzed using the analyzer having a narrow portion. In each of FIGS. 7A and 7B, the horizontal axis indicates the wavelength, and the vertical axis indicates the emission intensity (the number of counts). In FIG. 7A, the solid line shows the result obtained regarding the example, and the dashed line shows the result obtained regarding Comparative Example 1. In FIG. 7B, the solid line shows the result obtained regarding Comparative Example 2, and the dashed line shows the result obtained regarding Comparative Example 3. As can be seen from FIG. 7A, in the example, the number of counts at the mercury peak increased by about 900 counts as compared to Comparative Example 1. Also, as can be seen from FIG. 7B, in Comparative Example 2, the number of counts at 253.00 nm, which is near 253.65 nm as the wavelength of plasma emission characteristic of mercury, increased by about 500 counts as compared with Comparative Example 3. In FIG. 7B, the peak is observed at 253.00 nm. This is because the measured value includes a measurement error caused by the plasma spectrochemical analyzer for the resin cell measurement. From these results, it was found that the analysis method of the present invention can obtain the number of counts about twice as great as the number of counts obtained by the method using a resin cell having a narrow portion, even when the mercury concentration was 1/500. That is to say, these results demonstrate that the analysis method of the present invention achieves higher analytical sensitivity than the analysis methods disclosed in Patent Documents 2 and 3.

While the present invention has been described above with reference to embodiments and examples, the present invention is by no means limited thereto. Various changes that may become apparent to those skilled in the art may be made without departing from the scope of the present invention.

This application claims priority from Japanese Patent Application No. 2015-003795 filed on Jan. 13, 2015 and Japanese Patent Application No. 2016-003555 filed on Jan. 12, 2016. The entire disclosures of these Japanese Patent Applications are incorporated herein by reference.

INDUSTRIAL APPLICABILITY

The plasma spectrochemical analysis method of the present invention can be carried out easily and achieves high analytical sensitivity. Thus, according to the plasma spectrochemical analysis method of the present invention, it is possible to analyze a sample easily with high sensitivity without pretreating the sample, for example. Therefore, the present invention is very useful in its analysis of elements and the like utilizing plasma generation, for example.

EXPLANATION OF REFERENCE NUMERALS 1, 2: electrode
3: light transmitting part
4: container
5: light receiving part
6: insulating material
10: analyzer

What is claimed is:
1. A plasma spectrochemical analysis method comprising:
concentrating an analyte present in a sample where the sample is in contact with a pair of electrodes and the analyte is in a vicinity of at least one of the pair of electrodes by applying a first voltage to the pair of electrodes in the presence of the sample;
generating plasma by applying a second voltage to the pair of electrodes; and
detecting light emitted from the analyte excited by the plasma,
wherein the plasma generation and light detection steps are conducted in a liquid medium, and
wherein areas of contact of each of the pair of electrodes with the sample, the areas also being in contact with the liquid medium, are different from each other, and the electrode having a smaller contact area with the sample is used for analyzing the analyte by plasma generation.

2. The method according to claim 1, wherein the second voltage is higher than the first voltage.

3. The method according to claim 1, wherein the first voltage is at least 1 mV.

4. The method according to claim 1, wherein the second voltage is at least 10 V.

5. The method according to claim 1, wherein:
the pair of electrodes is disposed in a container,
the container comprises a light transmitting part, and
a light receiving part is disposed outside the container in such a manner that the light receiving part can receive light emitted from the analyte via the light transmitting part.

6. The method according to claim 1, wherein the analyte is a metal.

7. The method according to claim 6, wherein the metal is at least one selected from the group consisting of aluminum, antimony, arsenic, barium, beryllium, bismuth, cadmium, cesium, gadolinium, lead, mercury, nickel, palladium, platinum, tellurium, thallium, thorium, tin, tungsten, and uranium.

8. The method according to claim 1, wherein the sample is at least one of a biological sample and an environmental sample.

9. The method according to claim 8, wherein the biological sample is at least one selected from the group consisting of urine, blood, hair, saliva, sweat, and nails.

10. The method according to claim 8, wherein the environmental sample is at least one selected from the group consisting of foods, water, soil, and air.

11. The method according to claim 1, wherein the liquid medium is aqueous.

12. The method according to claim 11, wherein the aqueous medium is water or a buffer solution.

13. A plasma spectrochemical analyzer comprising:
a pair of electrodes;
a container having a bottomed cylindrical shape and a diameter of 1 to 5 cm and a height of 0.7 to 2 cm; and
a light receiving part,
wherein:
the container comprises a light transmitting part,
the pair of electrodes are disposed in the container and on different surfaces of the container, wherein one of the electrodes extends perpendicularly to the bottom surface of the container, the distance between the electrode tip and the bottom surface being from 0 to 2 cm, and
the light receiving part is disposed outside the container in such a manner that the light receiving part is capable of receiving via the light transmitting part light emitted from an excited target analyte present in a sample in a liquid medium.

14. The analyzer according to claim 13, wherein the light receiving part is a CCD or a transmission means for transmitting the emitted light to an optical measuring instrument disposed outside the analyzer.

15. The analyzer according to claim 13, wherein the light transmitting part is selected from the group consisting of quartz glass, acrylic resins (PMMA), borosilicate glass, polycarbonates (PC), cycloolefin polymers (COP), and methylpentene polymers.

16. The analyzer according to claim 13, wherein the analyte is a metal.

17. The analyzer according to claim 13, wherein the sample further contains a chelating agent or a masking agent.

18. The analyzer according to claim 13, wherein the liquid medium is aqueous.

\* \* \* \* \*